United States Patent [19]

Cregge et al.

[11] Patent Number: 4,622,422

[45] Date of Patent: Nov. 11, 1986

[54] CYCLOHEXANEALKANOIC ACIDS

[75] Inventors: Robert J. Cregge, Zionsville; Jeffrey S. Sabol, Indianapolis, both of Ind.

[73] Assignee: Merrell Dow Pharmaceuticals Inc., Cincinnati, Ohio

[21] Appl. No.: 768,769

[22] Filed: Aug. 23, 1985

[51] Int. Cl.$^4$ .................... C07C 149/26; A61K 31/16; A61K 31/19; A61K 31/215

[52] U.S. Cl. .................................. 562/507; 514/826; 560/125; 564/154

[58] Field of Search ........................ 562/507; 560/125; 564/154; 514/529, 574, 616

[56] References Cited

PUBLICATIONS

Chem. Abstracts, vol. 87, Abstract No. 84912f, 1977, Dronov et al., "Synthesis and Dehydration of Bis(-2-Hydroxyalkyl)sulfides".

J. Am. Chem. Soc., vol. 82, 1960, pp. 2511–2515, Dahehy et al., "The Relative Nucleophilic Character of Several Mercaptans Toward Ethylene Oxide".

Zhurnal Organicheskoi Khimii, vol. 3, No. 10, pp. 1735–1738, 1967, Shilov et al., "Reactions of Epoxy Compounds with Mercaptans".

*Primary Examiner*—Natalie Trousof
*Assistant Examiner*—Patricia M. Scott
*Attorney, Agent, or Firm*—John J. Kolano

[57] ABSTRACT

The present invention is directed to 2-hydroxy-4-alkylidenecyclohexanealkanoic acids having a mercaptoalkanoic acid substituent at the 3-position. Esters and amides corresponding to the acids referred to above are also encompassed by the present invention. These compounds are useful in the treatment of bronchial asthma and they are obtained by the reaction of an appropriate 2,3-epoxy-4-alkylidenecyclohexanealkanoate with a mercapto alkanoic acid ester in the presence of a tertiary amine. The indicated process gives the esters of the present invention which can be hydrolyzed to the corresponding free acids by standard procedures. The compounds described can be subjected to other known reactions to give the other compounds of the present invention.

9 Claims, No Drawings

CYCLOHEXANEALKANOIC ACIDS

The present invention relates to a group of compounds which are substituted cyclohexanealkanoic acids. More particularly, the present invention relates to compounds having the following general formula:

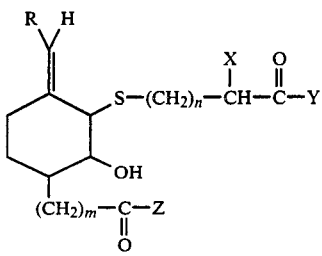

wherein m is an integer from 1 to 7 or m is an integer from 1 to 5; n is an integer from 0 to 2; R is a straight-chain alkyl containing from 8 to 15 carbon atoms; X is hydrogen or, when n is 1 or 2, X can be —NH$_2$; Y is hydroxy, —O—(lower alkyl), —NH$_2$, —NH(lower alkyl), or —N—(lower alkyl)$_2$ or

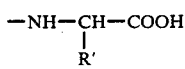

wherein R' is hydrogen, alkyl of 1 to 4 carbon atoms, or benzyl; and Z is hydroxy, —O—(lower alkyl), —NH$_2$, —NH—(lower alkyl), or —N— (lower alkyl)$_2$. The lower alkyl groups referred to above contain 1 to 4 carbon atoms.

Stereoisomerism is possible with the present compounds and the chemical structure as presented above is considered as encompassing all of the possible stereoisomers and also racemic mixtures of such stereoisomers. More specifically, where the substituent in the above structure is attached to the cyclohexane ring by a single bond, two isomers are possible at each point, depending on whether the substituent is above or below the plane of the cyclohexane ring. Such isomers are not possible when the substituent is attached to the ring by a double bond but, in that case, geometric (cis-trans) isomerism is possible, depending on the position of the R-group in the doubly-bonded substituent relative to the remainder of the molecule. Generally, racemic mixtures can be obtained more readily than individual optical isomers so that the compounds as described and obtained in the present application should be considered as racemic mixtures unless indicated otherwise. Where absolute configuration is specified for a compound, that indicates the major optical isomer present in what is generally a mixture containing a small amount of the enantiomer.

The lower alkyl groups, as indicated above, contain 1 to 4 carbon atoms and this same definition applies to any use of the term below. Examples for such alkyl groups are methyl, ethyl, propyl and butyl. Examples of the alkyl groups for R are octyl, nonyl, decyl, undecyl, dodecyl, tridecyl, tetradecyl and pentadecyl.

The therapeutically acceptable salts of the foregoing acids, i.e., where Y and/or Z are —OH, are also included within the scope of the present invention. These basic salts would include, but would not be limited to, sodium, potassium, calcium, magnesium, triethylamine, tromethamine, dicyclohexylamine and the like as is well-known in the art. Such base salts can be obtained by standard procedures using the free acids of the present invention and the appropriate base. The preferred compounds of the present invention, however, are those wherein both Y and Z are hydroxy.

As examples of compounds of the present invention are the following:

(1α,2β,3α,4E)-3-[(Carbamoylmethyl)thio]-2-hydroxy-4-tetradecylidenecyclohexaneacetamide.

(1α,2β,3α,4E)-3-[(N-Methylcarbamoylmethyl)thio]-2-hydroxy-N-methyl-4-tetradecylidenecyclohexaneacetamide.

(1α,2β,3α,4E)-3-[(N,N-Diethylcarbamoylmethyl)thio]-2-hydroxy-N,N-diethyl-4-tetradecylidenecyclohexaneacetamide.

(1α,2β,3α,4E)-3-[(Carboxymethyl)thio]-2-hydroxy-4-hexadecylidenecyclohexaneacetic acid.

(1α,2β,3α,4E)-3-[(Carboxymethyl)thio]-2-hydroxy-4-decylidenecyclohexaneacetic acid.

(1α,2β,3α,4E)-3-[(Carboxymethyl)thio]-2-hydroxy-4-tetradecylidenecyclohexanehexanoic acid.

(1α,2β,3α,4E)-3-[(Carboxymethyl)thio]-2-hydroxy-4-tetradecylidenecyclohexaneoctanoic acid.

(1α,2α,3β,4E)-3-[(3-Carboxypropyl)thio]-2-hydroxy-4-tetradecylidenecyclohexanepropionic acid.

(1α,2α,3β,4E)-3-[(2-Amino-2-carboxyethyl)thio]-2-hydroxy-4-tetradecylidenecyclohexanepropionic acid.

(1α,2β,3α,4E)-3-[[N-(Carboxymethyl)carbamoylmethyl]-thio]-2-hydroxy-4-tetradecylidenecyclohexaneacetic acid.

(1α,2β,3α,4E)-3-[[N-(1-Carboxybutyl)carbamoylmethyl)-thio]-2-hydroxy-4-tetradecylidenecyclohexaneacetic acid.

(1α,2β,3α,4E)-3-[[N-(1-Carboxy-2-phenylethyl)carbamo-ylmethyl]thio]-2-hydroxy-4-tetradecylidenecyclohexaneacetic acid.

The compounds of the present invention are prepared by reacting an epoxide of the formula:

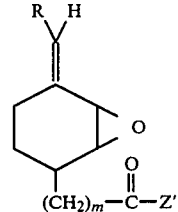

wherein m and R are defined as above and Z' is —O—(-lower alkyl), —NH$_2$, —NH(lower alkyl), or —N—(-lower alkyl)$_2$, with a mercaptoalkanoic acid derivative of the formula:

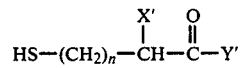

wherein n is an integer from 0 to 2; X' is hydrogen or, when n is 1 or 2, X' can be Q—NH— wherein Q is an amine-protecting group; Y' is —O—(lower alkyl), —NH$_2$, —NH(lower alkyl), —N—(lower alkyl)$_2$ or

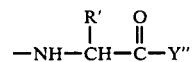

wherein R' is hydrogen, alkyl of 1 to 4 carbon atoms or benzyl and Y" is —O—(lower alkyl); in an appropriate solvent in the presence of base, optionally followed, when Y', Y" or Z' are —O— (lower alkyl), by treatment with a strong inorganic base followed by acidification with strong acid to give those compounds wherein Y, Y" or Z are —OH.

Although a protecting group is not specifically necessary when X is —NH$_2$, the amine group can be protected by one of the standard protecting groups in amino acids. Trifluoroacetyl is a preferred group for this purpose since it would be hydrolyzed at the same time as any Y or Z ester groups to leave a free amino group. Benzyloxycarbonyl is also a useful protecting group although the conditions necessary for hydrolysis are stronger than those for a trifluoroacetyl group. However, the benzyloxycarbonyl group can also be removed by catalytic hydrogenation without affecting any ester groups present elsewhere in the molecule.

The base used in the epoxide opening process is preferably a tertiary amine such triethylamine. The solvent used for the reaction should be one which dissolves the reactants but is inert with respect to the reaction itself. Lower alkanols are the preferred solvents and, particularly, lower alkanols which would correspond to the alcohol portion of any ester used in the reaction. Thus, methanol would be used in the case of methyl esters while ethanol would be used in the case of ethyl esters.

The subsequent saponification of the esters with a strong base followed by acidification of the resulting salt mixture to give the corresponding free acid are all standard procedures in organic chemistry so that it should not be necessary to elaborate on the reagents and reaction conditions used.

The process as described above gives those compounds wherein the hydroxy and the thio substituents on the cyclohexane ring bear a trans-relationship to each other. To obtain the compounds wherein the indicated substituents have a cis-relationship, it is necessary to carry out a further series of reactions starting with the trans-compounds. Thus, an appropriate trans-diester (before saponification to the acid) is oxidized using oxalyl chloride, dimethylsulfoxide and a tertiary amine such triethylamine in an inert solvent such as dichloromethane. In this reaction, the hydroxy group is oxidized to the corresponding ketone which is then reduced back to an alcohol using a reagent such as sodium borohydride in methanol. This reduction gives an alcohol with a configuration that is different from the original alcohol or it gives a mixture of epimeric alcohols which can be separated by standard procedures. Once the alcohol with the desired configuration is obtained in this way, any ester groups present in the molecule can be hydrolyzed in the same way as described previously.

The epoxides used as the starting materials in the general process described above can be obtained from available starting materials using an appropriate series of reactions. Thus, in one process, the hydroxy group in 2-cyclohexen-1-ol is protected with a tert-butyldiphenylsilyl group and the double bond is oxidized to the corresponding epoxide using a peroxide such as m-chloroperbenzoic acid. Treatment of the resulting epoxide with lithium diethylamide in ether brings about ring opening with introduction of a double bond to give 2-(tert-butyldiphenylsilyloxy)-5-cyclohexene-1-ol. This compound is then reacted with 1,1,1-triethoxyethane to introduce an acetic acid ester group by a Claisen rearrangement followed by removal of the silyl protecting group by means of tetra-n-butylammonium fluoride. An alkyl 4-hydroxycyclohex-2-eneacetate results from this process. The double bond in this compound is oxidized to the epoxide using an appropriate peroxide and the hydroxy group is oxidized to the ketone using oxalyl chloride and dimethylsulfoxide in the presence of a tertiary amine to give the corresponding epoxy ketone. This ketone is subjected to a Wittig reaction using an appropriate reagent to give the desired starting materials referred to earlier.

In another approach to the preparation of the intermediates desired, a 4-methoxybenzenealkanoic acid is used as the starting material. This is treated with lithium and ammonia in tert-butanol in an ether solvent to bring about partial reduction of the benzene ring and give 4-oxocyclohex-1-enepropionic acid. This acid is treated with an appropriate alkanol in the presence of a strong acid such as sulfuric acid to esterify the free acid to the corresponding ester and to isomerize the double bond into conjugation with the carbonyl of the cyclic ketone. The ketone is then reduced to the corresponding alcohol using sodium borohydride in methanol in the presence of cerium chloride followed by oxidation of the double bond to the corresponding epoxide using an appropriate peroxide. The resulting epoxyhydroxycyclohexanealkanoate is then oxidized using oxalyl chloride and dimethylsulfoxide in the presence of a tertiary amine such as triethylamine to convert the hydroxy group to the corresponding ketone and this ketone is subjected to a Wittig reaction with an appropriate reagent to give the epoxide desired as described previously.

In those instances where the final product desired is an amide, such compounds can be obtained by using the appropriate reagents in the procedures described above. Alternatively, the esters of the present invention obtained as described previously can be converted to the corresponding amides by reaction with ammonia or an appropriate amine.

The specific conditions used in the processes referred to above are described in more detail in the examples below.

The compounds of the present invention are useful in the treatment of allergic diseases and, particularly, in the treatment of bronchial asthma. Thus, SRS-A (slow-reacting substance of anaphylaxis) is known as a substance which is a very important mediator in allergic bronchial asthma. Specifically, SRS-A is a substance which is synthesized and released in or near target tissues, in a sensitive allergic subject, shortly after challenge by the appropriate antigen with the human bronchus being particularly sensitive to SRS-A. Thus, a substance which would counteract the effects of SRS-A would be useful in the treatment of bronchial asthma.

More recent studies have established that SRS-A is actually a mixture of substances which can be described as peptido-leukotrienes. LTD$_4$ is one of these leukotrienes and can be considered as representative of them so that antagonism of this specific substance would provide effects similar to the antagonism of SRS-A generally. Specifically, the compounds of the present invention are useful as antagonists of LTD$_4$ so that they are useful in the treatment of allergic diseases and, particularly in the treatment of bronchial asthma. The present compounds are selective in this antagonist activity in that they are not considered as competitive against histamine or carbachol.

The activity of the compounds of the present invention can be demonstrated by the following test procedures.

Longitudinal Muscle of Guinea Pig Ileum

Male, Hartley-Duncan, guinea pigs were sacrificed by cervical dislocation. The terminal portion of the ileum was removed, rinsed, and placed in Burn's modified Tyrode's solution. The longitudinal muscle was then carefully dissected from the circular muscle of the ileum. The longitudinal muscle was cut into 1-2 cm. segments which were placed in a tissue bath containing oxygenated Burn's modified Tyrode's solution warmed to 37° C. A tension of 1.0 gram was then placed on each segment of muscle. After equilibration for 1 hour, 1 μM Indomethacin was added to each bath. After 5 minutes, each tissue segment was then exposed to a concentration of 60 nM leukotriene $D_4$. This response was then considered to be the initial maximal contraction that each segment will produce. After washing the tissue several times, over a 1 hour period, 1 μM Indomethacin was again added to each bath. After a 5 minute period the test agent or vehicle was added to the bath. After 15 minutes, a concentration-response curve was generated using cumulatively increasing concentrations of leukotriene $D_4$. The concentration-response was then compared to the initial maximum contraction. A test compound was considered active, if at concentrations up to 100 μM, it produces a significant shift to the right of the concentration-response relationship to leukotriene $D_4$. The antagonist activity was quantitated in terms of a $pA_2$ value calculated according to the method described by Arunlakshana and Schild, (Brit. J. Pharmac. Chemotherap. 14; 48, 1959).

3H-LTD$_4$- Specific Receptor Binding in Guinea Pig Lung Membranes

Male guinea pigs were sacrificed and the lungs were removed and placed in ice cold 50 mM Tris-HCl buffer, pH 7.4. The lungs were then homogenized with a Polytron homogenizer and the homogenate was centrifuged at 1000 g for 10 minutes at 4° C. The supernatant was then centrifuged at 30,000 g for 15 minutes at 4° C. to obtain the membrane pellet. This pellet was resuspended in 50 mM Tris-HCl to provide the working suspension of lung membranes. Binding assays were then carried out in 50 mM Tris-HCl at pH 7.6 and 37° C. using incubation periods of 20-40 min. Separation of bound $^3$H-LTD$_4$ from free $^3$H-LTD$_4$ were performed by rapid vacuum filtration through Whatman GF/B glass fiber filters using ice cold Tris-HCl buffer and three 4 ml washes. Filtration and washing were completed in less than 8 seconds. The radioactivity on the filters was then measured. Specific binding of $^3$H-LTD$_4$ was defined as the binding of $^3$H-LTD$_4$ in the absence of unlabelled LTD$_4$ minus the binding of $^3$H-LTD$_4$ in the presence of $2 \times 10^{-7}$M unlabelled LTD$_4$. Specific binding of $^3$H-LTD$_4$ was 60-80% of total binding. Studies with test agents demonstrate the ability of the test compound to inhibit the specific binding of $^3$H-LTD$_4$. In these tests increasing concentrations of the agent are used to block the $^3$H-LTD$_4$ specific binding. The concentration that reduces the specific binding of $^3$H-LTD$_4$ by 50% is termed the IC$_{50}$.

The specific activity observed for some compounds of the present invention when tested by the above procedures is summarized in the table below. Variations in activity occur, however, and it appears that activity decreases with a decrease in the length of the R-alkyl groups from the tetradecylidene compounds included in the table.

| COMPOUND (EXAMPLE NO.) | G.P. ILEUM pA$_2$(LTD$_4$) | G.P. LUNG SPECIFIC BINDING IC$_{50}$, μM |
|---|---|---|
| 15A | 5.47 | 3 |
| 15E | 5.65 | — |
| 15B | 5.51 | 0.4 |
| 15C | 5.79 | — |
| 15D | 5.70 | — |
| 18 | 4.51 | — |

In Vivo Biological Activity

Compounds of the present invention were also tested for in vivo leukotriene D$_4$ antagonist activity in anesthetized guinea pigs using a modified Konzett-Rössler preparation. Specifically, the guinea pigs were anesthetized with sodium pentobarbital and surgically prepared for artificial ventilation by a constant volume respirator. The inflation pressure produced by the respirator was measured for each inflation of the guinea pigs' lungs. Increases in inflation pressure above baseline are indicative of bronchoconstriction. After establishing a baseline inflation pressure, the guinea pig was exposed for 1 minute to an aerosol generated ultrasonically from a 1 μg/ml solution of leukotriene D$_4$. After the inflation pressure returned to baseline, the guinea pig was exposed to an aerosol generated from a solution of a test compound. Ten to twenty minutes later, the guinea pig was re-exposed to a 1 minute aerosol generated from 1 μg/ml leukotriene D$_4$. This response was then compared to the initial response and the % inhibition of the response was determined. The results can be summarized as follows:

| TEST COMPOUND (EXAMPLE NO.) | PERCENT INHIBITION |
|---|---|
| 15B (5 mg/ml solution aerosolized) | 44.3% |
| 15A (5 mg/ml solution aerosolized) | 25.3% |
| 15A (10 mg/ml solution aerosolized) | 64.2% |

The compounds of the present invention may be administered either as individual therapeutic agents or as mixtures with other therapeutic agents. They may be administered alone but are generally administered in the form of pharmaceutical compositions, i.e., mixtures of the active agents with suitable pharmaceutical carriers or diluents. Examples of such compositions include tablets, lozenges, capsules, powders, aerosol sprays, aqueous or oily suspensions, syrups, elixirs and aqueous solutions for injection. The compounds are most preferably administered in oral dosage forms.

The nature of the pharmaceutical composition and the pharmaceutical carrier or diluent will, of course, depend on the desired route of administration, i.e., orally, parenterally or by inhalation. Oral compositions may be in the form of tablets or capsules and may contain conventional excipients such as binding agents (e.g., syrup, acacia, gelatin, sorbitol, tragacanth or polyvinylpyrrolidone), fillers (e.g., lactose, sugar, maize-starch, calcium phosphate, sorbitol or glycine), lubricants (e.g., magnesium stearate, talc, polyethylene glycol or silica), disintegrants (e.g., starch) or wetting agents (e.g., sodium lauryl sulfate). Oral liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as suspending agents, flavoring agents, diluents or emulsifying agents. For parenteral administration or inhalation, solutions or suspensions of a compound of the present invention with conventional pharmaceutical vehicles may be employed, e.g., as an aerosol spray for inhalation, as an aqueous solution for intravenous injection or as an oily suspension for intramuscular injection. The compounds may also be administered by means of inhalers or other devices which permit the active compounds in the form of dry powders to come into direct contact with the lungs. Procedures for the preparation of compositions as discussed above are described in standard texts, such as *Remington's Pharmaceutical Sciences*, Mack Publishing Company, Easton, Pa.

The compounds of the present invention or pharmaceutical compositions thereof may be administered to human asthmatic patients at dosages in the range from about 0.1 to about 40 mg/kg. Single oral doses of approximately 1–1000 mg of active ingredient and multiple oral doses totaling up to about 4000 mg/day of active ingredient can be used. When administered by inhalation, lower doses are generally given, i.e., on the order of about 0.1 of the normal dosage for the particular compound in question. These values are illustrative only, however, and the physician of course will ultimately determine the dosage most suitable for a particular patient on the basis of factors such as age, weight, diagnosis, severity of the symptoms and the particular agent to be administered.

The following examples are presented to illustrate the present invention but they should not be construed as limiting it in any way.

EXAMPLE 1

A solution of 5.0 g of 2-cyclohexen-1-ol, 7.6 g of imidazole and 14.6 ml of tert-butylchlorodiphenylsilane in 100 ml of N,N-dimethylformamide was stirred at room temperature for 16 hrs. The mixture was then partitioned between 100 ml of saturated brine and 250 ml of ether. The layers were separated and the organic layer was washed with 100 ml of water and dried over magnesium sulfate and the solvent was evaporated in vacuo to give 3-(tert-butyldiphenylsilyloxy)cyclohexene as a viscous oil which was used without further purification. $^1$H NMR (CDCl$_3$) δ 1.05 (s, 9H); 4.10 (m, 1H); 5.50 (br s, 2H); 7.20–7.70 (m, 10H).

A stirred solution of 17.1 g of 3-(tert-butyldiphenylsilyloxy)cyclohexene in 300 ml of dichloromethane was cooled in an ice-water bath and 11.1 g of m-chloroperoxybenzoic acid was added in one portion and the resulting mixture was stored in a refrigerator at 4° C. for 20 hours. The resulting mixture was then filtered to remove precipitated m-chlorobenzoic acid and the filtrate was washed successively with 100 ml of 1N aqueous sodium hydroxide, 100 ml of saturated brine, and 100 ml of water. The resulting solution was dried over magnesium sulfate and the solvent was evaporated in vacuo. Purification of the residue by means of a Waters Prep 500 LC (silica gel), 1:49 ethyl acetate-hexane) gave (1α,2α,3β)-1,2-epoxy-3-(tert-butyldiphenylsilyloxy)cyclohexane. $^1$H NMR (CDCl$_3$) δ 1.10 (s, 9H); 3.05 (m, 2H); 4.00 (m, 1H); 7.2–7.8 (m, 10H).

EXAMPLE 3

To a solution of 23.3 g of diethylamine in 600 ml of anhydrous ether, cooled in an ice-water bath, was added dropwise 117 ml of 2.7M n-butyllithium in hexane and the resulting yellow solution was stirred at 0° C. under a nitrogen atmosphere for 15 minutes. A solution of 45 g of (1α,2α,3β)-1,2-epoxy-3-(tert-butyldiphenylsilyloxy)cyclohexane in 100 ml of anhydrous ether was then added dropwise over 30 minutes. The cooling bath was removed and the mixture was allowed to warm to room temperature over a period of 1 hour and then refluxed for 18 hours. The mixture was then cooled 0° C., 100 ml of water was added, and the organic layer was separated and washed successively with 100 ml of 1N hydrochloric acid and 100 ml of saturated brine. It was then dried over magnesium sulfate and the solvent was evaporated in vacuo. Purification of the residue by means of a Waters Prep 500 LC (silica gel), 1:9 ethyl acetate-hexane) gave (1α,2β)-2-(tert-butyldiphenylsilyloxy)-5-cyclohexen-1-ol as a clear viscous oil. $^1$H NMR (CDCl$_3$) δ 1.08 (s, 9H); 3.71–3.78 (m, 1H); 4.14 (br s, 1H); 7.21–7.6 (m, 10H).

EXAMPLE 4

A mixture of 29.2 g of (1α,2β)-2-(tert-butyldiphenylsilyloxy)-5-cyclohexen-1-ol, 76 ml of triethyl orthoacetate, and 0.3 ml of propionic acid in 500 ml of o-xylene was heated in an oil bath at 138° C. for 48 hours. The mixture was cooled and volatile material was distilled off by means of bulb to bulb distillation (80°/2 mm Hg). The residual oil was purified by means of Waters Prep 500 LC (silica gel, 1:19 ethyl acetate-hexane) to give ethyl (1α,4β)-4-(tert-butyldiphenylsilyloxy)cyclohex-2-eneacetate. $^1$H NMR (CDCl$_3$) δ 1.05 (s, 9H); 1.15 (t, 3H); 4.00 (q, 2H); 4.00–4.20 (m, 1H); 5.45 (br s, 2H); 7.20–7.70 (m, 10H).

EXAMPLE 5

To a stirred solution of 16.3 g of ethyl (1α,4β)-4-(tert-butyldiphenylsilyloxy)cyclohex-2-eneacetate in 78 ml of tetrahydrofuran, cooled in an ice-water bath, was added dropwise 77 ml of 1M tetrabutylammonium fluoride over a period of 10 minutes. The cooling bath was removed and the mixture was allowed to warm to room temperature and stirred for 3 hours. The mixture was partitioned between 200 ml of water and 200 ml of ether and the 2 layers were separated. The aqueous layer was washed with 100 ml of ethyl acetate and the washing was combined with the original organic layer and dried over magnesium sulfate. The solvent was evaporated and the residue was purified by means of a Waters Prep 500 LC (silica gel, 1:4 ethyl acetate-hexane) to give ethyl (1α,4β)-4-hydroxycyclohex-2-eneacetate as an oil. $^1$H NMR (CDCl$_3$) δ 1.25 (t, 3H); 4.14 (q, 2H); 4.18–4.25 (m, 1H); 5.72 (dd, 2H).

EXAMPLE 6

A stirred solution of 4.2 g of ethyl (1α,4β)-4-hydroxycyclohex-2-eneacetate in 150 ml of dichloromethane was cooled in an ice-water bath and 5.1 g of m-chloroperoxybenzoic acid was added in one portion and the mixture was stored in a refrigerator at 4° C. for 20 hours. It was then filtered to remove precipitated m-chlorobenzoic acid and the filtrate was washed successively with 50 ml of cold 1N aqueous sodium hydroxide, 50 ml of saturated brine and 50 ml of water. It was then dried over magnesium sulfate and the solvent was evaporated to leave a residue which was purified by Waters Prep 500 LC (silica gel, 2:3 ethyl acetate-hexane) to give ethyl (1α,2β,3β,4β)-4-hydroxy-2,3-epoxycyclohexaneacetate as an oil. $^1$H NMR (CDCl$_3$) δ 4.40 (q, 2H); 4.22 (m, 1H); 3.56 (m, 1H); 3.40 (d, 1H); 1.30 (t, 3H).

Epoxidation of ethyl (1α,4β)-4-(tert-butyldiphenylsilyloxy)cyclohex-2-eneacetate by the procedure described above followed by removal of the silyl protecting group by the procedure described in Example 5 gave ethyl (1α,2α,3α,4β)-4-hydroxy-2,3-epoxycyclohexaneacetate.

EXAMPLE 7

To a solution of 1.5 ml of oxalyl chloride in 50 ml of dichloromethane, cooled to −65° C. in a dry ice-acetone bath, was added 2.6 ml of dimethylsulfoxide while keeping the temperature below −55° C. Stirring was continued for 10 minutes. A solution of 2.9 g of ethyl (1α,2β,3β,4β)-4-hydroxy-2,3-epoxycyclohexaneacetate in 10 ml of dichloromethane was added dropwise, the mixture was stirred at −65° to −60° C. for 20 minutes, and then 10.8 ml of triethylamine was added dropwise at −60° C. The cooling bath was removed and the mixture was allowed to warm to room temperature over a period of 1 hour. At the end of this time, 30 ml of water was added and the stirring was continued for 10 minutes. The two layers were separated and the aqueous layer was washed with 50 ml of dichloromethane. The washing was combined with the original organic layer and dried over magnesium sulfate and the solvent was evaporated. Purification of the residue by Waters Prep 500 LC gave ethyl (1α,2β,3β)-2,3-epoxy-4-oxocyclohexaneacetate as an oil. $^1$H NMR (CDCl$_3$) δ 4.18 (q, 2H); 3.54 (m, 1H); 3.24 (d, 1H); 2.85 (m, 1H); 1.28 (t, 3H).

Ethyl (1α,2α,3α)-2,3-epoxy-4-oxocyclohexaneacetate was also obtained by using the appropriate starting material and following the procedure described above.

Using the same procedure and the appropriate starting materials, the following additional compounds were obtained: Ethyl [1R-(1β,2α,3α)]-2,3-epoxy-4-oxocyclohexaneacetate, [α]$_D$ = +30°; Ethyl [1S-(1α,2β,3β)]-2,3-epoxy-4-oxocyclohexaneacetate, [α]$_D$ = −36°. The starting material for the first compound was obtained by starting with (S)-2-cyclohexen-1-ol and carrying out the reactions as described in Examples 1-6. (S)-2-Cyclohexen-1-ol and the processes of Examples 1-6 were also used to prepare the starting material for the second compound except that the process of the examples were carried out in the following order: Examples 2, 1, 3, 4, 6 and 5.

EXAMPLE 8

To a stirred solution of 4.4 g of 4-methoxybenzenepropionic acid and 75 ml of tert-butanol, 50 ml of tetrahydrofuran and 300 ml of liquid ammonia there was added 0.85 g of lithium wire in 2-3 cm pieces over a 10 minute period to give a mixture which had a persistent deep blue color. After an additional 10 minutes, 13.4 g of powdered ammonium chloride was added and the ammonia was allowed to evaporate. The residue was dissolved in 300 ml of water and washed twice with 200-ml portions of ether. The aqueous mixture was acidified with concentrated hydrochloric acid and extracted thoroughly with three 200-ml portions of ether. The combined organic layers were dried over magnesium sulfate and the solvent was evaporated to give 4-oxocyclohex-1-enepropionic acid as a clear oil. $^1$H NMR (CDCl$_3$) δ 2.20–2.80 (br m, 20H); 5.45 (m, 1H); 11.3 (br s, 1H).

EXAMPLE 9

A solution of 3.5 g of 4-oxocyclohex-1-enepropionic acid in 16.5 ml of methanol and 0.9 ml of concentrated sulfuric acid was refluxed for 30 minutes. The mixture was cooled and the solvent was evaporated under reduced pressure. The resulting residue was partitioned between 50 ml of 5% aqueous sodium bicarbonate and 100 ml of ether. The separated aqueous layer was washed twice with 100-ml portions of ether and the washings were combined with the original organic layer and dried over magnesium sulfate. The solvent was evaporated to give a crude product which was found to be a 1:1 mixture of double bond isomers by NMR analysis. Flash chromatography of this crude product (silica gel, 3:7 ethyl acetate-hexane) separated the compounds and gave methyl 4-oxocyclohex-2-enepropionate as a clear oil. $^1$H NMR (CDCl$_3$) δ 3.60 (s, 3H); 5.70–6.00 (dd, 1H); 6.60–6.95 (d of m, 1H).

EXAMPLE 10

To a mixture of 0.36 g of methyl 4-oxocyclohex-2-enepropionate and 500 ml of 0.4M cerium chloride in methanol there was added carefully 0.07 g of sodium borohydride and the mixture was stirred for 10 minutes at room temperature. The reaction was quenched with 2 ml of water and the methanol solvent was removed under reduced pressure. The residue was partitioned between 10 ml of water and 50 ml of ether and the separated organic layer was dried over magnesium sulfate. Evaporation of the solvent from the organic solution gave methyl 4-hydroxycyclohex-2-enepropionate as a clear oil which was used without further purification. $^1$H NMR (CDCl$_3$) δ 3.56 (s, 3H); 3.90–4.30 (m, 1H); 5.50–5.75 (m, 2H).

EXAMPLE 11

To a solution of 3.3 g of methyl 4-hydroxycyclohex-2-enepropionate in 75 ml of dichloromethane, cooled in an ice-water bath, was added 3.6 g of m-chloroperoxybenzoic acid in one portion and the mixture was stored in a refrigerator at 4° C. for 16 hours. It was filtered to remove precipitated m-chlorobenzoic acid and the filtrate was washed with 25 ml of 10% aqueous potassium carbonate. The aqueous washing was itself washed twiced with 25-ml portions of ether and the washings were combined with the original organic phase and dried over magnesium sulfate. Evaporation of the solvent under reduced pressure gave a residual oil which was purified by Waters Prep 500 LC to a 2:1 mixture of stereoisomers in which the major isomer was methyl 2,3-epoxy-4-hydroxycyclohexanepropionate. This mixture was used without further separation and showed the following spectral data. $^1$H NMR (CDCl$_3$) δ 2.85–3.30 (m, 2H); 3.55 (s, 3H); 3.75–4.00 (m, 1H).

EXAMPLE 12

To a solution of 0.36 ml of oxalyl chloride in 5 ml of dichloromethane, cooled to −65° C. in a dry ice-acetone bath, was added dropwise 0.6 ml of dimethyl sulfoxide while keeping the temperature below −55° C. Stirring was continued for 10 minutes. A solution of 0.69 g of the mixture of alcohols obtained in Example 11, and 5 ml of dichloromethane, was added dropwise, the mixture was stirred at −65° C. to −60° C. for 20 minutes and then 1.6 ml of triethylamine was added dropwise at −60° C. The cooling bath was removed and the mixture was allowed to warm to room temperature over a period of one hour. At the end of this time, 5 ml of water was added and stirring was continued for 10 minutes. The two layers were separated and the aqueous layer was washed with 10 ml of dichloromethane. The washing was combined with the original organic layer and dried over magnesium sulfate. Evaporation of the solvent gave a crude product which was a mixture of isomers. This was separated by flash chromatography (silica gel 3:7 ethyl acetate-hexane) to give methyl (1α,2α,3α)-2,3-epoxy-4-oxocyclohexanepropionate and methyl (1α,2β,3β)-2,3-epoxy-4-oxocyclohexanepropionate. The second compound was obtained as an oil which exhibited the following spectral data. $^1$H NMR (CDCl$_3$) δ 3.22 (d, 1H); 3.44 (m, 1H); 3.71 (s, 3H).

EXAMPLE 13

To a solution of 0.74 g of n-tetradecyltriphenylphosphonium bromide in 10 ml of anhydrous tetrahydrofuran, cooled to −35° C. in a dry ice-acetonitrile bath, was added 0.78 ml of 1.75M n-butyllithium in hexane and the resulting orange solution was stirred for 25 minutes, during which time a temperature of −42° C. was attained. To this mixture was added dropwise 0.27 g of ethyl (1α,2β,3β)-2,3-epoxy-4-oxocyclohexaneacetate in 5 ml of tetrahydrofuran and the resulting chalky white mixture was stirred for two hours at −42° C. to −35° C. The cooling bath was removed and the reaction was allowed to warm to room temperature. After two hours, 10 ml of saturated aqueous ammonium chloride was added and the tetrahydrofuran was removed under reduced pressure. The residue was extracted twice with 50-ml portions of ether and the combined organic layers were dried over magnesium sulfate. The solvent was evaporated and the residue was purified by Waters Prep 500 LC (silica gel, 1:30 ethyl acetate-hexane) to give ethyl (1α,2β,3β,4E)-2,3-epoxy-4-tetradecylidenecyclohexaneacetate as a waxy solid. $^1$H NMR (CDCl$_3$) δ 5.58 (br t, 2H); 3.71 (d, 1H); 3.20 (br d, 1H); 2.46–2.19 (m, 2H); 1.25 (br m, 22H); 0.88 (t, 3H).

The procedure described above was repeated using the appropriate alkyltriphenylphosphonium bromide and the appropriate 2,3-epoxy-4-oxocyclohexane. The exact procedure used can be varied to quench the reaction mixture with saturated aqueous sodium chloride instead of saturated aqueous ammonium chloride and extracting the mixture with ether without evaporating the tetrahydrofuran. In addition, the final purification can be carried out using flash chromatography (silica gel, 1:9 ethyl acetate-hexane). The following additional compounds were obtained:

Methyl (1α,2β,3β,4E)-2.3-epoxy-4-tetradecylidenecyclohexanepropionate as a solid melting at room temperature. $^1$H NMR (CDCl$_3$) δ 0.88 (s, 3H); 1.25 (br s, 22H); 2.45 (t, 2H); 3.25 (d, 1H); 3.70 (s, 3H); 3.70 (m, 1H); 5.60 (t, 1H).

Methyl (1α,2α,3α,4E)-2,3-epoxy-4-tetradecylidenecyclohexanepropionate as a solid melting at room temperature. $^1$H NMR (CDCl$_3$) δ 5.60 (t, 1H); 3.70 (s, 3H); 3.70 (m, 1H); 3.25 (d, 1H); 2.45 (t, 2H); 1.25 (br s, 22H); 0.88 (t, 3H).

Ethyl (1α,2α,3α,4E)-2,3-epoxy-4-tetradecylidenecyclohexaneacetate.

Ethyl (1α,2β,3β,4E)-2,3-epoxy-4-nonylidenecyclohexaneacetate.

Methyl (1α,2β,3β,4E)-2,3-epoxy-4-tetradecylidenecyclohexanebutyrate. The necessary starting material was obtained by starting with 4-methyloxybenzenebutyric acid and following the procedures of Examples 8–12.

Ethyl [1R-(1β,2α,3α,4E)]-2,3-epoxy-4-tetradecylidenecyclohexaneacetate, [α]$_D$=−39°.

Ethyl [1S-(1α,2β,3β,4E)]-2,3-epoxy-4-tetradecylidenecyclohexaneacetate, [α]$_D$=+33°.

EXAMPLE 14

A solution of 0.21 g of ethyl (1α,2β,3β,4E)-2,3-epoxy-4-tetradecylidenecyclohexaneacetate in 4 ml of absolute ethanol containing 0.22 ml of triethylamine was added to 0.12 ml of ethyl 2-mercaptoacetate and the mixture was stirred at room temperature for 16 hours. Volatile materials were removed under reduced pressure and the resulting residue was purified by using Waters Prep 500 LC (silica gel, 1:9 ethyl acetate-hexane) to give ethyl (1α,2β,3α,4E)-3-[[(ethoxycarbonyl)methyl]thio]-2-hydroxy-4-tetradecylidenecyclohexaneacetate as an oil. $^1$H NMR (CDCl$_3$) δ 5.45 (br t, 1H); 4.20 (q, 2H); 4.14 (q, 2H); 3.91 (br d, 1H); 3.79 (br q, 1H); 3.32–3.24 (m, 2H); 2.64–2.48 (m, 2H); 1.25 (m, 28H); 0.88 (t, 3H).

The above general procedure was repeated using similar reactants to give the corresponding products with the conditions being varied to use methanol as the solvent when the reactants were methyl esters and to use a slightly different proportion of ethyl acetate-hexane (1:4 or 1.5:8.5) in the final purification. In this way, the following compounds were obtained:

Ethyl (1α,2β,3α,4E)-3-[[2-(ethoxycarbonyl)ethyl]thio]-2-hydroxy-4-tetradecylidenecyclohexaneacetate as an oil. $^1$H NMR (CDCl$_3$) δ 5.41 (t, 1H); 4.20–4.08 (octet, 4H); 3.80–3.70 (m, 2H); 1.26 (m, 28H); 0.88 (t, 3H).

Methyl (1α,2β, 3β,4E)-3-[[(methoxycarbonyl)methyl]-thio]-2-hydroxy-4-tetradecylidenecyclohexanepropionate as an oil. $^1$H NMR (CDCl$_3$) δ 5.50 (t, 1H); 3.70 (s, 3H); 1.25 (br s, 22H); 0.90 (t, 3H).

Methyl (1α, 2α, 3β,4E)-3-[[2-(methoxycarbonyl)ethyl]thio]-2-hydroxy-4-tetradecylidenecyclohexanepropionate as an oil. $^1$H NMR (CDCl$_3$) δ 5.55 (t, 1H); 3.70 and 3.65 (2 s, 6H); 1.25 (br s, 22H); 0.90 (t, 3H).

Methyl (1α,2β,3α,4E)-3-[[(methoxycarbonyl)methyl]thio]-2-hydroxy-4-tetradecylidenecyclohexanepropionate as an oil. $^1$H NMR (CDCl$_3$) δ 0.88 (s, 3H); 1.25 (br s, 22H); 3.25 (s, 2H); 3.69 (s, 3H); 3.72 (s, 3H); 5.45 (t, 1H).

Methyl (1α,2β,3α,4E)-3-[[2-(methoxycarbonyl)ethyl]thio]-2-hydroxy-4-tetradecylidenecyclohexanepropionate.

Ethyl (1α,2α,3β,4E)-3-[[2-(ethoxycarbonyl)ethyl]thio]-2-hydroxy-4-tetradecylidenecyclohexaneacetate.

Ethyl (1α,2α,3β,4E)-3-[[(ethoxycarbonyl)methyl]thio]-2-hydroxy-4-tetradecylidenecyclohexaneacetate.

Ethyl (1α,2α,3α,4E)-3-[[2-(ethoxycarbonyl)ethyl]thio]-2-hydroxy-4-nonylidenecyclohexaneacetate.

Ethyl (1α,2β,3α,4E)-3-[[(ethoxycarbonyl)methyl]thio]-2-hydroxy-4-nonylidenecyclohexaneacetate.

Methyl (1α,2α,3α,4E)-3-[[(methoxycarbonyl)methyl]thio]-2-hydroxy-4-tetradecylidenecyclohexanebutyrate.

Ethyl [1R-(1β,2α,3β,4E)]-3-[[(ethoxycarbonyl)methyl]thio]-2-hydroxy-4-tetradecylidenecyclohexaneacetate, [α]$_D$=−39°.

Ethyl [1S-(1α,2β,3α,4E)]-3-[[(ethoxycarbonyl)methyl]thio]-2-hydroxy-4-tetradecylidenecyclohexaneacetate, [α]$_D$= −44°.

EXAMPLE 15A

A solution of 0.21 g of potassium hydroxide in 7 ml of methanol and 8 ml of water was added to 0.21 g of ethyl (1α,2β,3α,4E)-3-[[(ethoxycarbonyl)methyl]thio]-2-hydroxy-4-tetradecylidenecyclohexaneacetate and the mixture was stirred for 18 hours at room temperature. The resulting solution was then partitioned between 10 ml of water and 15 ml of ether and the layers were separated. The aqueous layer was acidified with 1 ml of 5N hydrochloric acid and extracted twice with 50-ml portions of ethyl acetate. The combined organic layers were dried over magnesium sulfate and the solvent evaporated to leave a waxy residue. This was recrystallized from 1:30 ethyl ether-hexane to give (1α,2β,3α,4E)-3-[(carboxymethyl)thio]-2-hydroxy-4-tetradecylidenecyclohexaneacetic acid as a white powder melting at about 79.5°–81.5° C. $^1$H NMR (CDCl$_3$) δ 5.3–6.2 (br s, 1H); 5.43 (t, 1H); 3.99 (dd, 1H); 3.84 (d, 1H); 3.42–3.34 (m, 2H); 2.69 (dd, 1H); 2.54 (dd, 1H); 2.36 (m, 1H); 2.07 (m, 3H); 1.85 (m, 1H); 1.49 (m, 1H); 1.25 (br s, 22H); 0.88 (t, 3H). This compound has the following structural formula:

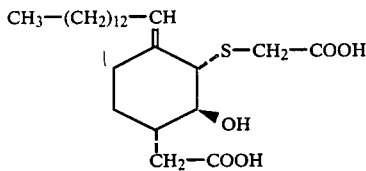

EXAMPLES 15B–15M

When the procedure of Example 15A was repeated using the appropriate starting materials, the following compounds were obtained:

B. (1α,2β,3α,4E)-3-[(2-Carboxyethyl)thio]-2-hydroxy-4-tetradecylidenecyclohexaneacetic acid as a white powder melting at about 86° C.–88° C. after recrystallization from 1:30 ethyl ether-hexane. $^1$H NMR (CDCl$_3$) δ 5.44 (br t, 1H); 3.90 (dd, 1H); 3.79 (d, 1H); 2.9–2.5 (br m, 6H); 1.25 (br s, 22H); 0.88 (t, 3H).

C. (1α,2α,3β,4E)-3-(Carboxymethyl)thio]-2-hydroxy-4-tetradecylidenecyclohexanepropionic acid as a clear oil. $^1$H NMR (CDCl$_3$) δ 5.51 (t, 1H); 1.30 (br s; 22H); 0.88 (t, 3H).

D. (1α,2α,3β,4E)-3-[(2-Carboxyethyl)thio]-2-hydroxy-4-tetradecylidenecyclohexanepropionic acid as an oil. $^1$H NMR (CDCl$_3$) δ 5.40 (t, 1H); 1.30 (br s, 22H); 0.88 (t, 3H).

E. (1α,2β,3α,4E)-3-[(Carboxymethyl)thio]-2-hydroxy-4-tetradecylidenecyclohexanepropionic acid as a white powder melting at about 85° C.–86° C. after recrystallization from hexane. $^1$H NMR (CDCl$_3$) δ 0.88 (s, 3H); 1.25 (br s, 22H); 3.45–3.60 (dd, 2H); 4.02 (d, 1H); 4.35 (m, 1H); 5.41 (t, 1H).

F. (1α,2β,3α,4E)-3-[(Carboxyethyl)thio]-2-hydroxy-4-tetradecylidenecyclohexanepropionic acid as a white powder melting at about 87.7°–88.2° C. after recrystallization from 1:30 ethyl ether-hexane. $^1$H NMR (CDCl$_3$) δ 5.40 (t, 1H); 4.30 (m, 1H); 3.85 (d, 1H); 2.9–2.5 (br m, 6H); 1.25 (br s, 22H); 0.90 (t, 3H).

G. (1α,2α,3β,4E)-3-[(Carboxyethyl)thio]-2-hydroxy-4-tetradecylidenecyclohexaneacetic acid as a clear oil. $^1$H NMR (CDCl$_3$) δ 5.51 (t, 1H); 4.50 (s, 1H); 4.30 (s, 1H); 4.00 (s, 1H); 2.9–2.5 (br m, 5H); 1.30 (br s, 22H); 0.90 (t, 3H).

H. (1α,2α,3β,4E)-3-[(Carboxymethyl)thio]-2-hydroxy-4-tetradecylidenecyclohexaneacetic acid as a white powder melting at about 108°–111.5° C. after recrystallization from 1:30 ethyl ether-hexane. $^1$H NMR (CDCl$_3$) δ 5.57 (t, 1H); 4.51 (m, 2H); 3.27 (s, 2H); 1.25 (br s, 22H); 0.88 (t, 3H).

I. (1α,2β,3α,4E)-3-[(2-Carboxyethyl)thio]-2-hydroxy-4-nonylidenecyclohexaneacetic acid as a white powder melting at about 77°–78.5° C. after crystallization from 1:30 ethyl ether-hexane. $^1$H NMR (CDCl$_3$) δ 5.41 (t, 1H); 3.90 (t, 1H); 3.79 (d, 1H); 2.89–2.51 (m, 5H); 1.25 (br s, 14H); 0.88 (t, 3H).

J. (1α,2β,3α,4E)-3-[(Carboxymethyl)thio]-2-hydroxy-4-nonylidenecyclohexaneacetic acid as a white powder melting at about 96°–98° C. after crystallization from 1:30 ethyl ether-hexane. $^1$H NMR (CDCl$_3$) δ 5.42 (t, 1H); 4.04 (m, 1H); 3.80 (m, 1H); 3.44 (q, 1H); 1.27 (br s, 14H); 0.88 (t, 3H).

K. (1α,2β,3α,4E)-3-[(Carboxymethyl)thio]-2-hydroxy-4-tetradecylidenecyclohexanebutyric acid as a white powder melting at about 72.5°–74° C. after recrystallization from 1:20 ethyl ether-hexane. $^1$H NMR (CDCl$_3$) δ 5.45 (t, 1H); 3.88 (s, 2H); 3.31 (dd, 2H); 1.25 (br s, 22H); 0.88 (t, 3H).

L. (+)-[1R-(1β,2α,3β,4E)-3-[(Carboxymethyl)thio]-2-hydroxy-4-tetradecylidenecyclohexaneacetic acid as a white powder melting at about 76°–80° C. after crystallization from 1:30 ethyl ether-hexane. $^1$H NMR (CDCl$_3$) δ 5.44 (t, 1H); 3.88 (br s, 1H); 3.78 (m, 1H); 3.28 (q, 2H); 1.25 (br s, 22H); 0.88 (t, 3H); [α]$_D^{20}$= +48°; (~74% e.e.).

M. (−)-[1S-(1α,2β,3α,4E)-3-[(Carboxymethyl)thio]-2-hydroxy-4-tetradecylidenecyclohexaneacetic acid as a white powder melting at about 76°–78.5° C. after recrystallization from 1:30 ethyl ether-hexane. $^1$H NMR (CDCl$_3$) δ 5.43 (t, 1H); 4.03 (dd, 1H); 3.81 (d, 1H); 3.41 (q, 2H); 1.25 (br s, 22H); 0.88 (t, 3H); [α]$_D^{20}$= −60°; (~90% e.e.).

EXAMPLE 16

To a solution of 0.11 ml of oxalyl chloride in 10 ml of dichloromethane, cooled to −65° C. in a dry ice-acetone bath, was added 0.19 ml of dimethylsulfoxide while keeping the temperature below −55° C. Stirring was continued for 10 minutes. A solution of 0.48 g of methyl (1α,2β,3α,4E)-3-[[(methoxycarbonyl)methyl]thio]-2-hydroxy-4-tetradecylidenecyclohexaneacetate in 5 ml of dichloromethane was added dropwise and the mixture was stirred at −65° C. to −60° C. for 20 minutes. Then, 0.79 ml of triethylamine was added dropwise at −60° C. The cooling bath was removed and the mixture was then allowed to warm to room temperature over a period of one hour. At the end of this time, 5 ml of water was added and stirring was continued for 10 minutes. The two layers were separated and the aqueous layer was washed with 20 ml of dichloromethane. The dichloromethane washing was combined with the original organic layer and dried over magnesium sulfate. The solvent was evaporated and the residue was purified by means of Waters Prep 500 LC (silica gel, 1:9 ethyl acetate-hexane) to give methyl (1α,3α,4E)-3-[[(methoxycarbonyl)methyl]thio]-2-oxo-4-tetradecylidenecyclohexaneacetate as an oil. $^1$H NMR (CDCl$_3$) δ 5.47 (t, 1H); 4.42 (s, 1H); 3.74 and 3.69 (2s, 6H); 3.29–3.25 (d, 2H); 2.77 (m, 1H); 1.25 (br s, 22H); 0.88 (t, 3H).

EXAMPLE 17

Sodium borohydride (0.01 g) was added in one portion to a mixture of 0.25 g of methyl (1α,3α,4E)-3-[[(methoxycarbonyl)methyl]thio]-2-oxo-4-tetradecylidenecyclohexaneacetate and 5 ml of methanol and this was stirred at room temperature for 15 minutes. The solvent was then removed under reduced pressure and the residue was partitioned between 10 ml of water and 25 ml of ether. The organic layer was separated and dried over magnesium sulfate and the solvent was evaporated to leave a crude oily product. This was purified by means of Waters Prep 500 LC (silica gel, 1:4 ethyl acetate-hexane) to give methyl (1α,2α,3α,4E)-3-[[(methoxycarbonyl)methyl]thio]-2-hydroxy-4-tetradecylidenecyclohexaneacetate as an oil. $^1$H NMR (CDCl$_3$) δ 5.31 (t, 1H); 4.22 (d, 1H); 3.74 and 3.68 (2(s), 6H); 3.36 (m, 1H); 3.31–3.27 (d, 2H); 1.28 (br s, 22H); 0.88 (t, 3H).

EXAMPLE 18

A solution of 0.19 g of potassium hydroxide in 4 ml of ethanol and 2.5 ml of water was added to 0.11 g of methyl (1α,2α,3α,4E)-3-[[(methoxycarbonyl)methyl]thio]-2-hydroxy-4-tetradecylidenecyclohexaneacetate and the mixture was stirred for 18 hours at room temperature. The solution was then partitioned between 10 ml of water and 15 ml of ether and the layers were separated. The aqueous layer was cooled in an ice-water bath and acidified with 1 ml of 5N hydrochloric acid at 0° C. The acidified mixture was extracted twice with 40-ml portions of ethyl acetate and the combined organic extracts were dried over magnesium sulfate. The solvent was evaporated to leave a residual white solid which was recrystallized from 1:30 ethyl etherhexane to give (1α,2α,3α,4E)-3-[(carboxymethyl)thio]-2-hydroxy-4-tetradecylidenecyclohexaneacetic acid as a white powder melting at about 124°–127° C. $^1$H NMR (CDCl$_3$) δ 5.28 (t, 1H); 4.26 (d, 1H); 3.29 (s, 6H); 3.21–3.03 (dd, 2H); 1.25 (s, 22H); 0.88 (t, 3H).

What is claimed is:

1. A compound of the formula:

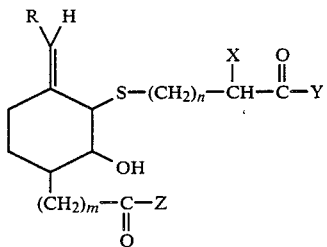

wherein m is an integer from 1 to 5; n is an integer from 0 to 2; R is straight-chain alkyl containing from 8 to 15 carbon atoms; X is hydrogen or, when n is 1 or 2, X can be —NH$_2$; Y is hydroxy, —O—(lower alkyl), —NH$_2$, —NH(lower alkyl), —N—(lower alkyl)$_2$ or —NHCH$_2$COOH; and Z is hydroxy, —O—(lower alkyl), —NH$_2$, —NH—(lower alkyl), or —N—(lower alkyl)$_2$ and Z is the same as Y except that, when Y is —NHCH$_2$COOH, Z is hydroxy.

2. A compound according to claim 1 which has the formula:

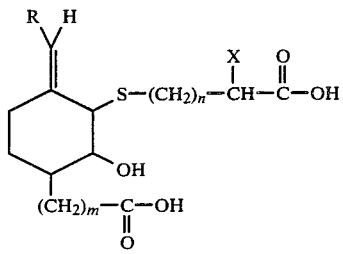

wherein m is an integer from 1 to 5; n is an integer from 0 to 2; R is straight-chain alkyl containing from 8 to 15 carbon atoms; and X is H or, when n is 1 or 2, X can be —NH$_2$.

3. A compound according to claim 1 which has the formula:

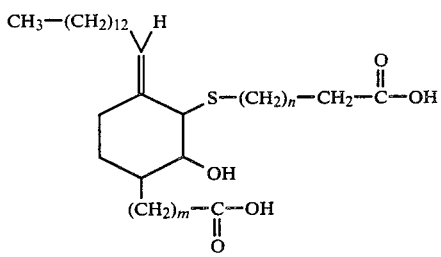

wherein m is an integer from 1 to 5; and n is an integer from 0 to 2.

4. A compound according to claim 1 which is (1α,2β,3α,4E)-3-[(carboxymethyl)thio]-2-hydroxy-4-tetradecylidenecyclohexaneacetic acid.

5. A compound according to claim 1 which is (1α,2β,3α,4E)-3-[(2-carboxyethyl)thio]-2-hydroxy-4-tetradecylidenecyclohexaneacetic acid.

6. A compound according to claim 1 which is (1α,2α,3β,4E)-3-[(carboxymethyl)thio]-2-hydroxy-4-tetradecylidenecyclohexanepropionic acid.

7. A compound according to claim 1 which is (1α,2α,3β,4E)-3-[(2-carboxyethyl)thio]-2-hydroxy-4-tetradecylidenecyclohexanepropionic acid.

8. A compound according to claim 1 which is (1α,2β,3α,4E)-3-[(carboxymethyl)thio]-2-hydroxy-4-tetradecylidenecyclohexanepropionic acid.

9. A compound according to claim 1 which is (1α,2α,3α,4E)-3-[(carboxymethyl)thio]-2-hydroxy-4-tetradecylidenecyclohexaneacetic acid.

* * * * *

UNITED STATES PATENT AND TRADEMARK OFFICE
CERTIFICATE OF CORRECTION

PATENT NO. : 4,622,422

DATED : November 11, 1986

INVENTOR(S) : Robert J. Cregge, et al

It is certified that error appears in the above-identified patent and that said Letters Patent is hereby corrected as shown below:

Column 12, line 68, "-39°." should read -- +39°. --.

Signed and Sealed this

Twenty-fourth Day of January, 1989

Attest:

DONALD J. QUIGG

Attesting Officer

Commissioner of Patents and Trademarks